United States Patent [19]
Everhart et al.

[11] Patent Number: 5,173,288
[45] Date of Patent: Dec. 22, 1992

[54] NAIL POLISH REMOVER COMPRISING ACETONE AND HYDROLYZED KERATIN

[75] Inventors: Nelson S. Everhart, Unionville; Peter Gallagher, Richmond Hill; Ellen J. M. Watts, North York, all of Canada

[73] Assignee: Chesebrough-Pond's USA Co., Greenwich, Conn.

[21] Appl. No.: 700,656

[22] Filed: May 15, 1991

[30] Foreign Application Priority Data

May 15, 1990 [GB] United Kingdom ................ 9010853

[51] Int. Cl.$^5$ .................... A61K 7/047; C11D 1/94
[52] U.S. Cl. ................................ 424/61; 424/401; 252/546; 252/364; 134/38
[58] Field of Search ................................ 424/401, 61

[56] References Cited

U.S. PATENT DOCUMENTS

| | | | |
|---|---|---|---|
| 3,124,825 | 3/1964 | Iovenko | 424/401 |
| 3,729,569 | 4/1973 | Charle | 424/401 |
| 4,445,521 | 5/1984 | Grollier | 424/47 |
| 4,485,037 | 11/1984 | Curtis | 424/401 |
| 4,824,662 | 4/1989 | Hofmann | 424/61 |

Primary Examiner—Thurman K. Page
Assistant Examiner—Raj Bawa
Attorney, Agent, or Firm—Milton L. Honig

[57] ABSTRACT

An aqueous acetone-based nail polish remover comprises:
i. from 40 to 90% by weight acetone, and
ii. from 0.001 to 10% by weight of hydrolyzed keratin.

8 Claims, No Drawings

NAIL POLISH REMOVER COMPRISING ACETONE AND HYDROLYZED KERATIN

FIELD OF INVENTION

The invention relates to an improved aqueous acetone-based nail polish remover.

BACKGROUND TO THE INVENTION

Nail polish is readily removed with pure acetone. However, acetone alone has a severe dehydrating effect upon skin, finger and toe nails, which is irritating to the former and renders the latter susceptible to cracking and breaking. Therefore, acetone-based commercial nail polish removers all contain other ingredients, e.g., water and/or oils, which lower this dehydrating effect but with the inevitable consequence that the efficacy of the polish remover is lowered. For example, Cutex (registered Trade Mark), a well known acetone-based polish remover, has about 80% of the polish removal efficacy of pure acetone. Several other commercial brands, e.g., Quickie Instant (registered Trade Mark), Unpolish (registered Trade Mark), and Dip It (registered Trade Mark), have substantially less.

It would be desirable if the nail water removal activity of aqueous acetone based polish removers which have high polish removal efficacy, e.g., those containing at least about 80% acetone and which have at least half the water removal activity of pure acetone, could be substantially lowered without adversely affecting their polish removal efficacy. To date, no such polish remover formulation is known to exist. It is an object of this invention to provide an aqueous acetone-based nail polish remover having high polish remover efficacy but less nail water removal activity than corresponding conventional polish removers. It is another object to provide a method of removing nail polish employing the novel polish removers of this invention.

SUMMARY OF THE INVENTION

The invention concerns an aqueous acetone-based nail polish remover comprising an effective amount of hydrolysed keratin, preferably together with an effective amount of lanolin or a derivative thereof, particularly an ethoxylated lanolin derivative. The hydrolysed keratin functions to reduce substantially the nail water removal activity of the polish remover; this benefit is further improved when the lanolin, or a derivative thereof, is also present.

The invention also relates to a method of removing nail polish by employing a polish remover of the invention.

DEFINITION OF THE INVENTION

Accordingly, the invention provides an aqueous acetone-based nail polish remover which comprises:

i. from 40 to 90% by weight acetone, and
ii. from 0.001 to 10% by weight of hydrolysed keratin.

DISCLOSURE OF THE INVENTION

The nail polish remover of the invention comprises an amount of acetone sufficient at least partially to remove nail polish from nails to which a polish has been applied.

The amount of acetone present in the nail polish remover of the invention is from 40 to 90%, preferably from 50 to 80% by weight of the nail polish remover.

The nail polish remover of the invention also comprises hydrolysed keratin, whose function is to reduce the amount of moisture loss from the nail following application of the remover, the water loss being due essentially to the presence of acetone in the nail polish remover.

The amount of hydrolysed keratin present in the nail polish remover of the invention is from 0.001 to 10%, preferably from 0.005 to 1% by weight of the nail polish remover.

The nail polish remover according to the invention preferably also comprises lanolin or a derivative thereof, whose function is further to reduce moisture loss from the nail following topical application of the nail polish remover to nails from which polish is to be removed.

A preferred lanolin derivative for use in accordance with the invention is PPG-12-PEG-50 lanolin, available, for example, as Lanexol AWS (ex Croda).

The amount of lanolin or derivative thereof when present in the nail polish remover of the invention is up to 20%, preferably from 1 to 20%, and most preferably from 2 to 10% by weight of the nail polish remover.

Other Ingredients

The nail polish remover of the invention can optionally also comprise a cosmetically acceptable water-soluble amine salt of a fatty acid amide of a hydrolysed collagen having the structure (1):

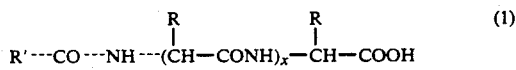

wherein R is the side chain of a primary or α-amino acid polymer unit of the hydrolysed collagen, x is the integer from 20 to 40, and R'—CO— is acyl radical of the amidizing fatty acid of from 5 to 18 carbon atoms.

Preferably the nail polish remover of the invention comprises up to 0.15%, preferably from 0.01 to 0.15% by weight of water-soluble amine salt of the fatty acid amide of a hydrolysed collagen.

The nail polish remover of the invention can also optionally comprise a cosmetically acceptable acid addition salt of a mono-fatty acid-amido substituted-trialkylamine cationic surfactant.

Preferably the nail polish remover comprises from 0.1 to 0.8% by weight of the acid addition salts of a mono-fatty acid-amido substituted-trialkylamine cationic surfactant.

The nail polish remover of the invention can also optionally comprise other ingredients conventionally employed in nail polish removers. These include solvents in addition to acetone, for example, isopropylalcohol, colouring agents, perfumes, viscosity raising agents, other emollients, moisture impermeable film formers such as nitrocellulose.

Evidence to Demonstrate Superiority of the Nail Varnish Remover of the Invention A panel of 13 women who conventially use nail varnish was selected.

All panellists removed their original nail varnish and then reapplied to the finger nails of each hand fresh varnish supplied to them. The fresh varnish was provided from the Cutex range, each panellist being given a bottle from the same batch.

20 minutes after application, when the varnish had thoroughly dried, the nail varnish was removed using either of the following two formulations, the 'Test' formulation being applied to the nails of one hand and the 'control' to the nails of the other.

| Ingredient | % w/w | |
|---|---|---|
| | TEST (#1) | CONTROL (#2) |
| Acetone | 54.0 | 54.0 |
| Isopropyl alcohol | 33.0 | 33.0 |
| Water | 9.0 | 9.1 |
| Hydrolysed animal keratin[1] | 0.1 | — |
| PPG-12-PEG-50 Lanolin | 2.5 | 2.5 |
| Cocamidopropyl dimethylamine propionate[2] | 0.5 | 0.5 |
| Aminomethylpropanol salt of isostearic hydrolysed collagen[3] | 0.1 | 0.1 |
| Fragrance and colour | 0.8 | 0.8 |

[1]Crotein ASK: 10–15% solution in alcohol (ex Croda)
[2]EMCOL 1655 (ex Emery)
[3]CROTEIN AD (ex Croda)

Each panellist was asked to complete a questionnaire indicating preferences against a list of attributes. The cumulative results are set out in Table 1 below:

TABLE 1

Nail Polish Remover Test
"Please remove the nail polish from the nails of your left hand with sample #1 and the nail polish from the nails of your right hand with #2".

| Compare #1 with #2 | #1 preferred | #2 preferred | No preference |
|---|---|---|---|
| *effectiveness at removing nail polish | 6 | 3 | 4 |
| *feel of nail after use (smoothness, softness) | 9 | 2 | 2 |
| *fragrance | 8 | 4 | 1 |
| *whitening of nail+ | 6 | 3 | 4 |
| Do you have any overall preference? | 9 | 3 | 1 |

Note: +the less whitening the better the product.

From these results, it was concluded that there was an overwhelming preference for the Test product #1 which contained hydrolysed animal keratin. Of the individual attributes reported on, the preference for feel of nail after use was most marked, this being perhaps the most important consumer perceivable attribute. Also, the after use fragrance was clearly superior with the Test product, indicating a more pronounced delivery and substantivity to the nail of the fragrance carried by the Test nail varnish remover.

EXAMPLES

The invention is further illustrated with reference to the following example.

EXAMPLE 1

A nail polish remover in accordance with the invention contained the following ingredients:

| Ingredient | % w/w |
|---|---|
| Acetone | 54.0 |
| Isopropyl alcohol | 33.0 |
| Water | 9.0 |
| Hydrolysed animal keratin[1] | 0.1 |

-continued

| Ingredient | % w/w |
|---|---|
| PPG-12-PEG-50 Lanolin | 2.5 |
| Cocamidopropyl dimethylamine propionate[2] | 0.5 |
| Aminomethylpropanol salt of isostearic hydrolysed collagen[3] | 0.1 |
| Fragrance and colour | 0.8 |

[1]Crotein ASK 10–15% solution in alcohol (ex Croda)
[2]EMCOL 1655 (ex Emery)
[3]CROTEIN AD (ex Croda)

What is claimed is:

1. An aqueous acetone-based nail polish remover which comprises:
   i. from 40 to 90% by weight acetone, and
   ii. from 0.001 to 10% by weight of hydrolysed keratin.

2. The nail polish remover according to claim 1, which comprises from 50 to 80% by weight acetone.

3. The nail polish remover according to claim 1, which comprises from 0.005 to 1% by weight of hydrolysed keratin.

4. The nail polish remover according to claim 1, which further comprises from 1 to 20% by weight of lanolin or a derivative thereof.

5. The nail polish remover according to claim 4, in which the lanolin derivative is PPG-12-PEG-50 lanolin.

6. The nail polish remover according to claim 1, which further comprises a cosmetically acceptable water-soluble amine salt of a fatty acid amide of a hydrolysed collagen having the structure (1)

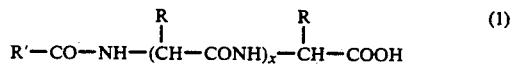

wherein R is the side chain of a primary or α-amino acid polymer unit of the hydrolysed collagen, x is an integer of from 20 to 40, and R'—CO— is acyl radical of the amidizing fatty acid having from 5 to 18 carbon atoms.

7. The nail polish remover according to claim 1, which further comprises a cosmetically acceptable acid addition salt of a mono-fatty acid-amido substituted-trialkylamine cationic surfactant.

8. The nail polish remover according to claim 1, which comprises:
   i. from 0 to 80% by weight of acetone,
   ii. from 0.001 to 1% by weight of hydrolysed keratin,
   iii. from 1 to 5% by weight of PPG-12-PEG-50 lanolin,
   iv. from 0.01 to 0.15% by weight of a cosmetically acceptable water-soluble amine salt of a fatty acid amide of hydrolysed collagen having the structure (1)

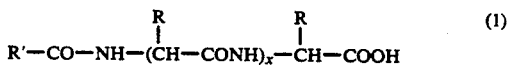

wherein R is the side chain of a primary or α-amino acid polymer unit of the hydrolysed collagen, x is the integer from 20 to 40, and R'—CO— is acyl radical of the amidizing fatty acid having from 5 to 18 carbon atoms, and
   v. from 0.1 to 0.8% by weight of cosmetically acceptable acid addition salt of a mono-fatty acid-amido substituted-trialkylamine cationic surfactant.

* * * * *